(12) United States Patent
Rose-John

(10) Patent No.: US 7,112,436 B1
(45) Date of Patent: *Sep. 26, 2006

(54) CONJUGATE FOR MODIFYING INTERACTIONS BETWEEN PROTEINS

(75) Inventor: Stefan Rose-John, Mainz (DE)

(73) Assignee: Angewandte Gentechnologie Systeme GmbH, Heidelberg (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/142,471

(22) PCT Filed: Mar. 7, 1997

(86) PCT No.: PCT/DE97/00458

§ 371 (c)(1),
(2), (4) Date: Nov. 11, 1998

(87) PCT Pub. No.: WO97/32891

PCT Pub. Date: Sep. 12, 1997

(30) Foreign Application Priority Data

Mar. 7, 1996 (DE) ............................. 196 08 813

(51) Int. Cl.
*C12N 5/16* (2006.01)
*C07K 14/54* (2006.01)

(52) U.S. Cl. ............. 435/325; 435/320.1; 435/254.21; 435/69.1; 530/350; 530/351; 536/23.4; 536/23.5; 424/192.1

(58) Field of Classification Search ................ 530/350, 530/351; 536/23.5, 24.2; 435/320.1, 252.3; 514/2

See application file for complete search history.

(56) References Cited

U.S. PATENT DOCUMENTS 5,260,203 A 11/1993 Ladner et al. ........... 435/172.3

FOREIGN PATENT DOCUMENTS

WO 95 15341 6/1995
WO 96 04314 2/1996
WO WO 96/04314 * 2/1996

OTHER PUBLICATIONS

Sui, X. et al, gp130 and c-Kit signalings synergize for ex vivo expansion of human primitive hemopoietic cells. PNAS. vol. 92, pp. 2859-2863.*
Davis et al., Science, vol. 259, Mar. 1993.*
Science News Report (Science 269, p. 1050, col. 2, paragraph 1, lines 6-15).*
Anderson (Scientific American, Sep. 1995, pp. 124-128).*
Blau et al. The New England Journal of Medicine, Nov. 2, 1995, p. 1204, col. 1-2 bridging sentences and p. 1205, col. 1-2, bridging paragraph and p. 1207, second column.*
Taga et al., Cell, vol. 58, pp. 573-581, 1989.*
Wang et al. (Nuc. Acids Res. 27: 4609-4618, 1999; p. 4617).*
Kaufman et al (Blood 94: 3178-3184, 1999).*
Wigley et al. Reprod Fert Dev 6: 585-588, 1994.*
Campbell et al. Theriology 47(1): 63-72, 1997.*
Phillips, A., J Pharm Pharmacology 53: 1169-1174, 2001.*
Stoyan T. et al, "Recombinant soluble human interleukin-6 receptor", European Journal of Biochemistry, Bd. 216, Nr. 1, Aug. 11, 1993, Seiten 239-245, XP002047601.
Ehlers M. et al, "Identification of Two Novel Regions of Human IL-6 Responsible for Receptor Biding and Signal Transduction", Journal of Immunology, Bd. 153, Nr. 4, Aug. 15, 1994, Seiten 1744-1753, XP000565715.
Sui, X. et al, "gp130 and c-Kit signalings synergize for ex vivo expansion of human primitive hemopoietic progenitor cells", Proceedings of the National Academy of Sciences of USA., Bd. 92, Mar. 1995, Washington, US, Seiten 2859-2863, XP002047602.
Fischer, M. et al, "A bioactive designer cytokine for human hematopoetic progenitor cell expansion" Nature Biotechnology, Bd. 15, Nr. 2, Feb. 1997, UBLISHING US, Seiten 142-145, XP002047603.
Fischer et al., "A bioactive designer cytokine for human hematopoietic progenitor cell expansion", *Nature Biotechnology*, Feb. 1997, pp. 142-145; vol. 15.

* cited by examiner

*Primary Examiner*—Eileen B. O'Hara
(74) *Attorney, Agent, or Firm*—Buchanan Ingersoll PC.

(57) ABSTRACT

The present invention concerns a conjugate comprising two polypeptides with a mutual affinity, the polypeptides being connected with each other via a linker. This invention also concerns the use of such a conjugate to influence interactions between proteins.

10 Claims, 4 Drawing Sheets

```
  1   GTCGACGCATGGAGTGGTAGCCGAGGAGGAAGC ATG CTG GCC GTC GGC TGC GCG CTG CTG GCT   63
  1                                     M   L   A   V   G   C   A   L   L   A    10

64  GCC CTG CTG GCC GCG CCG GGA GCG GCG CTG GCC CCA AGG CGC TGC CCT GCG CAG GAG GTG  123
 11   A   L   L   A   A   P   G   A   A   L   A   P   R   R   C   P   A   Q   E   V   30

124  GCA AGA GGC GTG CTG ACC AGT CTG CCA GGA GAC AGC GTG ACT CTG ACC TGC CCG GGG GTA  183
 31   A   R   G   V   L   T   S   L   P   G   D   S   V   T   L   T   C   P   G   V   50

184  GAG CCG GAA GAC AAT GCC ACT GTT CAC TGG GTG CTC AGG AAG CCG GCT GCA GGC TCC CAC  243
 51   E   P   E   D   N   A   T   V   H   W   V   L   R   K   P   A   A   G   S   H   70

244  CCC AGC AGA TGG GCT GGC ATG GGA AGG AGG CTG CTG CTG AGG TCG GTG CAG CTC CAC GAC  303
 71   P   S   R   W   A   G   M   G   R   R   L   L   L   R   S   V   Q   L   H   D   90

304  TCT GGA AAC TAT TCA TGC TAC CGG GCC GGC CGC CCA GCT GGG ACT GTG CAC TTG CTG GTG  363
 91   S   G   N   Y   S   C   Y   R   A   G   R   P   A   G   T   V   H   L   L   V  110

364  GAT GTT CCC CCC GAG GAG CCC CAG CTC TCC TGC TTC CGG AAG AGC CCC CTC AGC AAT GTT  423
111   D   V   P   P   E   E   P   Q   L   S   C   F   R   K   S   P   L   S   N   V  130

424  GTT TGT GAG TGG GGT CCT CGG AGC ACC CCA TCC CTG ACG ACA AAG GCT GTG CTC TTG GTG  483
131   V   C   E   W   G   P   R   S   T   P   S   L   T   T   K   A   V   L   L   V  150

484  AGG AAG TTT CAG AAC AGT CCG GCC GAA GAC TTC CAG GAG CCG TGC CAG TAT TCC CAG GAG  543
151   R   K   F   Q   N   S   P   A   E   D   F   Q   E   P   C   Q   Y   S   Q   E  170

544  TCC CAG AAG TTC TCC TGC CAG TTA GCA GTC CCG GAG GGA GAC AGC TCT TTC TAC ATA GTG  603
171   S   Q   K   F   S   C   Q   L   A   V   P   E   G   D   S   S   F   Y   I   V  190

604  TCC ATG TGC GTC GCC AGT AGT GTC GGG AGC AAG TTC AGC AAA ACT CAA ACC TTT CAG GGT  663
191   S   M   C   V   A   S   S   V   G   S   K   F   S   K   T   Q   T   F   Q   G  210

664  TGT GGA ATC TTG CAG CCT GAT CCG CCT GCC AAC ATC ACA GTC ACT GCC GTG GCC AGA AAC  723
211   C   G   I   L   Q   P   D   P   P   A   N   I   T   V   T   A   V   A   R   N  230

724  CCC CGC TGG CTC AGT GTC ACC TGG CAA GAC CCC CAC TCC TGG AAC TCA TCT TTC TAC AGA  783
231   P   R   W   L   S   V   T   W   Q   D   P   H   S   W   N   S   S   F   Y   R  250

784  CTA CGG TTT GAG CTC AGA TAT CGG GCT GAA CGG TCA AAG ACA TTC ACA ACA TGG ATG GTC  843
251   L   R   F   E   L   R   Y   R   A   E   R   S   K   T   F   T   T   W   M   V  270

844  AAG GAC CTC CAG CAT CAC TGT GTC ATC CAC GAC GCC TGG AGC GGC CTG AGG CAC GTG GTG  903
271   K   D   L   Q   H   H   C   V   I   H   D   A   W   S   G   L   R   H   V   V  290

904  CAG CTT CGT GCC CAG GAG GAG TTC GGG CAA GGC GAG TGG AGC GAG TGG AGC CCG GAG GCC  963
291   Q   L   R   A   Q   E   E   F   G   Q   G   E   W   S   E   W   S   P   E   A  310

964  ATG GGC ACG CCT TGG ACA GAA TCC AGG AGT CCT CCA GCT CGA GGA GGT GGA GGT TCT GGA 1023
311   M   G   T   P   W   T   E   S   R   S   P   P   A   R   G   G   G   G   S   G  330

1024 GGT GGA GGT TCT GGA GGT GGA GGT TCT GTC GAG CCA GTA CCC CCA GGA GAA GAT TCC AAA 1083
331   G   G   G   S   G   G   G   G   S   V   E   P   V   P   P   G   E   D   S   K  350

1084 GAT GTA GCC GCC CCA CAC AGA CAG CCA CTC ACC TCT TCA GAA CGA ATT GAC AAA CAA ATT 1143
351   D   V   A   A   P   H   R   Q   P   L   T   S   S   E   R   I   D   K   Q   I  370

1144 CGG TAC ATC CTC GAC GGC ATC TCA GCC CTG AGA AAG GAG ACA TGT AAC AAG AGT AAC ATG 1203
371   R   Y   I   L   D   G   I   S   A   L   R   K   E   T   C   N   K   S   N   M  390

1204 TGT GAA AGC AGC AAA GAG GCA CTG GCA GAA AAC AAC CTG AAC CTT CCA AAG ATG GCT GAA 1263
391   C   E   S   S   K   E   A   L   A   E   N   N   L   N   L   P   K   M   A   E  410

1264 AAA GAT GGA TGC TTC CAA TCT GGA TTC AAT GAG GAG ACT TGC CTG GTG AAA ATC ATC ACT 1323
411   K   D   G   C   F   Q   S   G   F   N   E   E   T   C   L   V   K   I   I   T  430

1324 GGT CTT TTG GAG TTT GAG GTA TAC CTA GAG TAC CTC CAG AAC AGA TTT GAG AGT AGT GAG 1383
431   G   L   L   E   F   E   V   Y   L   E   Y   L   Q   N   R   F   E   S   S   E  450

1384 GAA CAA GCC AGA GCT GTG CAG ATG AGT ACA AAA GTC CTG ATC CAG TTC CTG CAG AAA AAG 1443
451   E   Q   A   R   A   V   Q   M   S   T   K   V   L   I   Q   F   L   Q   K   K  470

1444 GCA AAG AAT CTA GAT GCA ATA ACC ACC CCT GAC CCA ACC ACA AAT GCC AGC CTG CTG ACG 1503
471   A   K   N   L   D   A   I   T   T   P   D   P   T   T   N   A   S   L   L   T  490

1504 AAG CTG CAG GCA CAG AAC CAG TGG CTG CAG GAC ATG ACA ACT CAT CTC ATT CTG CGC AGC 1563
491   K   L   Q   A   Q   N   Q   W   L   Q   D   M   T   T   H   L   I   L   R   S  510

1564 TTT AAG GAG TTC CTG CAG TCC AGC CTG AGG GCT CTT CGG CAA ATG TAG CATGGGCACCGTCGAC 1627
511   F   K   E   F   L   Q   S   S   L   R   A   L   R   Q   M   *                   525
```

[SEQ ID NO:1 and SEQ ID NO:2]

FIG. 1

```
  1 GTCGACGC ATG GAG TGG TAG CCGAGGAGGAAGC ATG CTG GCC GTC GGC TGC GCG CTG CTG GCT    63
  1                                         M   L   A   V   G   C   A   L   L   A    10

64 GCC CTG CTG GCC GCG CCG GGA GCG GCG CTG GCC CCA AGG CGC TGC CCT GCG CAG GAG GTG  123
 11  A   L   L   A   A   P   G   A   A   L   A   P   R   R   C   P   A   Q   E   V   30

124 GCA AGA GGC GTG CTG ACC AGT CTG CCA GGA GAC AGC GTG ACT CTG ACC TGC CCG GGG GTA  183
 31  A   R   G   V   L   T   S   L   P   G   D   S   V   T   L   T   C   P   G   V   50

184 GAG CCG GAA GAC AAT GCC ACT GTT CAC TGG GTG CTC AGG AAG CCG GCT GCA GGC TCC CAC  243
 51  E   P   E   D   N   A   T   V   H   W   V   L   R   K   P   A   A   G   S   H   70

244 CCC AGC AGA TGG GCT GGC ATG GGA AGG AGG CTG CTG CTG AGG TCG GTG CAG CTC CAC GAC  303
 71  P   S   R   W   A   G   M   G   R   R   L   L   L   R   S   V   Q   L   H   D   90

304 TCT GGA AAC TAT TCA TGC TAC CGG GCC GGC CGC CCA GCT GGG ACT GTG CAC TTG CTG GTG  363
 91  S   G   N   Y   S   C   Y   R   A   G   R   P   A   G   T   V   H   L   L   V  110

364 GAT GTT CCC CCC GAG GAG CCC CAG CTC TCC TGC TTC CGG AAG AGC CCC CTC AGC AAT GTT  423
111  D   V   P   P   E   E   P   Q   L   S   C   F   R   K   S   P   L   S   N   V  130

424 GTT TGT GAG TGG GGT CCT CGG AGC ACC CCA TCC CTG ACG ACA AAG GCT GTG CTC TTG GTG  483
131  V   C   E   W   G   P   R   S   T   P   S   L   T   T   K   A   V   L   L   V  150

484 AGG AAG TTT CAG AAC AGT CCG GCC GAA GAC TTC CAG GAG CCG TGC CAG TAT TCC CAG GAG  543
151  R   K   F   Q   N   S   P   A   E   D   F   Q   E   P   C   Q   Y   S   Q   E  170

544 TCC CAG AAG TTC TCC TGC CAG TTA GCA GTC CCG GAG GGA GAC AGC TCT TTC TAC ATA GTG  603
171  S   Q   K   F   S   C   Q   L   A   V   P   E   G   D   S   S   F   Y   I   V  190

604 TCC ATG TGC GTC GCC AGT AGT GTC GGG AGC AAG TTC AGC AAA ACT CAA ACC TTT CAG GGT  663
191  S   M   C   V   A   S   S   V   G   S   K   F   S   K   T   Q   T   F   Q   G  210

664 TGT GGA ATC TTG CAG CCT GAT CCG CCT GCC AAC ATC ACA GTC ACT GCC GTG GCC AGA AAC  723
211  C   G   I   L   Q   P   D   P   P   A   N   I   T   V   T   A   V   A   R   N  230

724 CCC CGC TGG CTC AGT GTC ACC TGG CAA GAC CCC CAC TCC TGG AAC TCA TCT TTC TAC AGA  783
231  P   R   W   L   S   V   T   W   Q   D   P   H   S   W   N   S   S   F   Y   R  250

784 CTA CGG TTT GAG CTC AGA TAT CGG GCT GAA CGG TCA AAG ACA TTC ACA ACA TGG ATG GTC  843
251  L   R   F   E   L   R   Y   R   A   E   R   S   K   T   F   T   T   W   M   V  270

844 AAG GAC CTC CAG CAT CAC TGT GTC ATC CAC GAC GCC TGG AGC GGC CTG AGG CAC GTG GTG  903
271  K   D   L   Q   H   H   C   V   I   H   D   A   W   S   G   L   R   H   V   V  290

904 CAG CTT CGT GCC CAG GAG GAG TTC GGG CAA GGC TGG TGG AGC GAG TGG AGC CCG GAG GCC  963
291  Q   L   R   A   Q   E   E   F   G   Q   G   W   W   S   E   W   S   P   E   A  310

964 ATG GGC ACG CCT TGG ACA GAA TCC AGG AGT CCT CCA GCT CGA GGA GGT GGA GGT TCT GGA 1023
311  M   G   T   P   W   T   E   S   R   S   P   P   A   R   G   G   G   G   S   G  330

1024 GGT GGA GGT TCT GTC GAG CCA GTA CCC CCA GGA GAA GAT TCC AAA GAT GTA GCC GCC CCA 1083
331   G   G   G   S   V   E   P   V   P   P   G   E   D   S   K   D   V   A   A   P  350

1084 CAC AGA CAG CCA CTC ACC TCT TCA GAA CGA ATT GAC AAA CAA ATT CGG TAC ATC CTC GAC 1143
351   H   R   Q   P   L   T   S   S   E   R   I   D   K   Q   I   R   Y   I   L   D  370

1144 GGC ATC TCA GCC CTG AGA AAG GAG ACA TGT AAC AAG AGT AAC ATG TGT GAA AGC AGC AAA 1203
371   G   I   S   A   L   R   K   E   T   C   N   K   S   N   M   C   E   S   S   K  390

1204 GAG GCA CTG GCA GAA AAC AAC CTG AAC CTT CCA AAG ATG GCT GAA AAA GAT GGA TGC TTC 1263
391   E   A   L   A   E   N   N   L   N   L   P   K   M   A   E   K   D   G   C   F  410

1264 CAA TCT GGA TTC AAT GAG GAG ACT TGC CTG GTG AAA ATC ATC ACT GGT CTT TTG GAG TTT 1323
411   Q   S   G   F   N   E   E   T   C   L   V   K   I   I   T   G   L   L   E   F  430

1324 GAG GTA TAC CTA GAG TAC CTC CAG AAC AGA TTT GAG AGT AGT GAG GAA CAA GCC AGA GCT 1383
431   E   V   Y   L   E   Y   L   Q   N   R   F   E   S   S   E   E   Q   A   R   A  450

1384 GTG CAG ATG AGT ACA AAA GTC CTG ATC CAG TTC CTG CAG AAA AAG GCA AAG AAT CTA GAT 1443
451   V   Q   M   S   T   K   V   L   I   Q   F   L   Q   K   K   A   K   N   L   D  470

1444 GCA ATA ACC ACC CCT GAC CCA ACC ACA AAT GCC AGC CTG CTG ACG AAG CTG CAG GCA CAG 1503
471   A   I   T   T   P   D   P   T   T   N   A   S   L   L   T   K   L   Q   A   Q  490

1504 AAC CAG TGG CTG CAG GAC ATG ACA ACT CAT CTC ATT CTG CGC AGC TTT AAG GAG TTC CTG 1563
491   N   Q   W   L   Q   D   M   T   T   H   L   I   L   R   S   F   K   E   F   L  510

1564 CAG TCC AGC CTG AGG GCT CTT CGG CAA ATG TAG C ATG GGC ACC GTC GAC               1612
511   Q   S   S   L   R   A   L   R   Q   M   *                                     520
```
[SEQ ID NO:3 and SEQ ID NO:4]

FIG. 2

```
Met Asn Ser Phe Ser Thr Ser Ala Phe Gly Pro Val Ala Phe Ser Leu
                                                      1
Gly Leu Leu Leu Val Leu Pro Ala Ala Phe Pro Ala Pro Val Pro Pro

Gly Glu Asp Ser Lys Asp Val Ala Ala Pro His Arg Gln Pro Leu Thr
 5               10              15                          20
Ser Ser Glu Arg Ile Asp Lys Gln Ile Arg Tyr Ile Leu Asp Gly Ile
                 25              30                          35
Ser Ala Leu Arg Lys Glu Thr Cys Asn Lys Ser Asn Met Cys Glu Ser
             40              45              50
Ser Pro Glu Ala Leu Ala Glu Asn Asn Leu Asn Leu Pro Lys Met Ala
         55              60              65
Glu Lys Asp Gly Cys Phe Gln Ser Gly Phe Asn Glu Glu Thr Cys Leu
     70              75              80
Val Lys Ile Ile Thr Gly Leu Leu Glu Phe Glu Val Tyr Leu Glu Tyr
 85              90              95                         100
Leu Gln Asn Arg Phe Glu Ser Ser Glu Glu Gln Ala Arg Ala Val Gln
                105             110                         115
Met Ser Thr Lys Val Leu Ile Gln Phe Leu Gln Lys Lys Ala Lys Asn
            120             125             130
Leu Asp Ala Ile Thr Thr Pro Asp Pro Thr Thr Asn Ala Ser Leu Leu
            135             140             145
Thr Lys Leu Gln Ala Gln Asn Gln Trp Leu Glu Asp Met Pro Thr His
    150             155             160
Leu Ile Leu Arg Ser Leu Lys Glu Phe Leu Gln Arg Ser Leu Arg Ala
165             170             175                         180
Leu Arg Gln Met
            184
```

[SEQ ID NO:5]

SEQUENCE LISTING

<160> NUMBER OF SEQ ID NOS: 17

<210> SEQ ID NO 1
<211> LENGTH: 1627
<212> TYPE: DNA
<213> ORGANISM: Unknown

```
<220> FEATURE:
<221> NAME/KEY: sig_peptide
<222> LOCATION: (34)..(90)
<220> FEATURE:
<221> NAME/KEY: mat_peptide
<222> LOCATION: (91)..(1608)
<220> FEATURE:
<221> NAME/KEY: CDS
<222> LOCATION: (34)..(1608)
<220> FEATURE:
<223> OTHER INFORMATION: Description of Unknown Organism:A conjugate
      comprising two polypeptides with a mutual
      affinity.

<400> SEQUENCE: 1
```

| | | | | | | | | | | | | | | | | |
|---|---|---|---|---|---|---|---|---|---|---|---|---|---|---|---|---|
| gtcgacgcat | ggagtggtag | ccgaggagga | agc | atg | ctg | gcc | gtc | ggc | tgc | gcg | | | | | | 54 |
| | | | | Met | Leu | Ala | Val | Gly | Cys | Ala | | | | | | |
| | | | | | | | | | | -15 | | | | | | |
| ctg | ctg | gct | gcc | ctg | ctg | gcc | gcg | ccg | gga | gcg | gcg | ctg | gcc | cca | agg | 102 |
| Leu | Leu | Ala | Ala | Leu | Leu | Ala | Ala | Pro | Gly | Ala | Ala | Leu | Ala | Pro | Arg | |
| | -10 | | | | -5 | | | | | -1 | 1 | | | | | |
| cgc | tgc | cct | gcg | cag | gag | gtg | gca | aga | ggc | gtg | ctg | acc | agt | ctg | cca | 150 |
| Arg | Cys | Pro | Ala | Gln | Glu | Val | Ala | Arg | Gly | Val | Leu | Thr | Ser | Leu | Pro | |
| 5 | | | | 10 | | | | | 15 | | | | | 20 | | |
| gga | gac | agc | gtg | act | ctg | acc | tgc | ccg | ggg | gta | gag | ccg | gaa | gac | aat | 198 |
| Gly | Asp | Ser | Val | Thr | Leu | Thr | Cys | Pro | Gly | Val | Glu | Pro | Glu | Asp | Asn | |
| | | 25 | | | | | 30 | | | | | 35 | | | | |
| gcc | act | gtt | cac | tgg | gtg | ctc | agg | aag | ccg | gct | gca | ggc | tcc | cac | ccc | 246 |
| Ala | Thr | Val | His | Trp | Val | Leu | Arg | Lys | Pro | Ala | Ala | Gly | Ser | His | Pro | |
| | | | 40 | | | | | 45 | | | | | 50 | | | |
| agc | aga | tgg | gct | ggc | atg | gga | agg | agg | ctg | ctg | ctg | agg | tcg | gtg | cag | 294 |
| Ser | Arg | Trp | Ala | Gly | Met | Gly | Arg | Arg | Leu | Leu | Leu | Arg | Ser | Val | Gln | |
| | 55 | | | | | 60 | | | | | 65 | | | | | |
| ctc | cac | gac | tct | gga | aac | tat | tca | tgc | tac | cgg | gcc | ggc | cgc | cca | gct | 342 |
| Leu | His | Asp | Ser | Gly | Asn | Tyr | Ser | Cys | Tyr | Arg | Ala | Gly | Arg | Pro | Ala | |
| | 70 | | | | | 75 | | | | | 80 | | | | | |
| ggg | act | gtg | cac | ttg | ctg | gtg | gat | gtt | ccc | ccc | gag | gag | ccc | cag | ctc | 390 |
| Gly | Thr | Val | His | Leu | Leu | Val | Asp | Val | Pro | Pro | Glu | Glu | Pro | Gln | Leu | |
| 85 | | | | 90 | | | | | 95 | | | | | 100 | | |
| tcc | tgc | ttc | cgg | aag | agc | ccc | ctc | agc | aat | gtt | gtt | tgt | gag | tgg | ggt | 438 |
| Ser | Cys | Phe | Arg | Lys | Ser | Pro | Leu | Ser | Asn | Val | Val | Cys | Glu | Trp | Gly | |
| | | | 105 | | | | | 110 | | | | | 115 | | | |
| cct | cgg | agc | acc | cca | tcc | ctg | acg | aca | aag | gct | gtg | ctc | ttg | gtg | agg | 486 |
| Pro | Arg | Ser | Thr | Pro | Ser | Leu | Thr | Thr | Lys | Ala | Val | Leu | Leu | Val | Arg | |
| | | 120 | | | | | 125 | | | | | 130 | | | | |
| aag | ttt | cag | aac | agt | ccg | gcc | gaa | gac | ttc | cag | gag | ccg | tgc | cag | tat | 534 |
| Lys | Phe | Gln | Asn | Ser | Pro | Ala | Glu | Asp | Phe | Gln | Glu | Pro | Cys | Gln | Tyr | |
| | 135 | | | | | 140 | | | | | 145 | | | | | |
| tcc | cag | gag | tcc | cag | aag | ttc | tcc | tgc | cag | tta | gca | gtc | ccg | gag | gga | 582 |
| Ser | Gln | Glu | Ser | Gln | Lys | Phe | Ser | Cys | Gln | Leu | Ala | Val | Pro | Glu | Gly | |
| | 150 | | | | | 155 | | | | | 160 | | | | | |
| gac | agc | tct | ttc | tac | ata | gtg | tcc | atg | tgc | gtc | gcc | agt | agt | gtc | ggg | 630 |
| Asp | Ser | Ser | Phe | Tyr | Ile | Val | Ser | Met | Cys | Val | Ala | Ser | Ser | Val | Gly | |
| 165 | | | | 170 | | | | | 175 | | | | | 180 | | |
| agc | aag | ttc | agc | aaa | act | caa | acc | ttt | cag | ggt | tgt | gga | atc | ttg | cag | 678 |
| Ser | Lys | Phe | Ser | Lys | Thr | Gln | Thr | Phe | Gln | Gly | Cys | Gly | Ile | Leu | Gln | |
| | | | 185 | | | | | 190 | | | | | 195 | | | |
| cct | gat | ccg | cct | gcc | aac | atc | aca | gtc | act | gcc | gtg | gcc | aga | aac | ccc | 726 |
| Pro | Asp | Pro | Pro | Ala | Asn | Ile | Thr | Val | Thr | Ala | Val | Ala | Arg | Asn | Pro | |
| | | 200 | | | | | 205 | | | | | 210 | | | | |
| cgc | tgg | ctc | agt | gtc | acc | tgg | caa | gac | ccc | cac | tcc | tgg | aac | tca | tct | 774 |
| Arg | Trp | Leu | Ser | Val | Thr | Trp | Gln | Asp | Pro | His | Ser | Trp | Asn | Ser | Ser | |
| | 215 | | | | | 220 | | | | | 225 | | | | | |

```
ttc tac aga cta cgg ttt gag ctc aga tat cgg gct gaa cgg tca aag      822
Phe Tyr Arg Leu Arg Phe Glu Leu Arg Tyr Arg Ala Glu Arg Ser Lys
    230                 235                 240 aca ttc aca aca tgg atg gtc aag gac ctc cag cat cac tgt gtc atc      870
Thr Phe Thr Thr Trp Met Val Lys Asp Leu Gln His His Cys Val Ile
245                 250                 255                 260 cac gac gcc tgg agc ggc ctg agg cac gtg gtg cag ctt cgt gcc cag      918
His Asp Ala Trp Ser Gly Leu Arg His Val Val Gln Leu Arg Ala Gln
                265                 270                 275 gag gag ttc ggg caa ggc gag tgg agc gag tgg agc ccg gag gcc atg      966
Glu Glu Phe Gly Gln Gly Glu Trp Ser Glu Trp Ser Pro Glu Ala Met
            280                 285                 290 ggc acg cct tgg aca gaa tcc agg agt cct cca gct cga gga ggt gga     1014
Gly Thr Pro Trp Thr Glu Ser Arg Ser Pro Pro Ala Arg Gly Gly Gly
        295                 300                 305 ggt tct gga ggt gga ggt tct gga ggt gga ggt tct gtc gag cca gta     1062
Gly Ser Gly Gly Gly Gly Ser Gly Gly Gly Gly Ser Val Glu Pro Val
    310                 315                 320 ccc cca gga gaa gat tcc aaa gat gta gcc gcc cca cac aga cag cca     1110
Pro Pro Gly Glu Asp Ser Lys Asp Val Ala Ala Pro His Arg Gln Pro
325                 330                 335                 340 ctc acc tct tca gaa cga att gac aaa caa att cgg tac atc ctc gac     1158
Leu Thr Ser Ser Glu Arg Ile Asp Lys Gln Ile Arg Tyr Ile Leu Asp
                345                 350                 355 ggc atc tca gcc ctg aga aag gag aca tgt aac aag agt aac atg tgt     1206
Gly Ile Ser Ala Leu Arg Lys Glu Thr Cys Asn Lys Ser Asn Met Cys
            360                 365                 370 gaa agc agc aaa gag gca ctg gca gaa aac aac ctg aac ctt cca aag     1254
Glu Ser Ser Lys Glu Ala Leu Ala Glu Asn Asn Leu Asn Leu Pro Lys
        375                 380                 385 atg gct gaa aaa gat gga tgc ttc caa tct gga ttc aat gag gag act     1302
Met Ala Glu Lys Asp Gly Cys Phe Gln Ser Gly Phe Asn Glu Glu Thr
    390                 395                 400 tgc ctg gtg aaa atc atc act ggt ctt ttg gag ttt gag gta tac cta     1350
Cys Leu Val Lys Ile Ile Thr Gly Leu Leu Glu Phe Glu Val Tyr Leu
405                 410                 415                 420 gag tac ctc cag aac aga ttt gag agt agt gag gaa caa gcc aga gct     1398
Glu Tyr Leu Gln Asn Arg Phe Glu Ser Ser Glu Glu Gln Ala Arg Ala
                425                 430                 435 gtg cag atg agt aca aaa gtc ctg atc cag ttc ctg cag aaa aag gca     1446
Val Gln Met Ser Thr Lys Val Leu Ile Gln Phe Leu Gln Lys Lys Ala
            440                 445                 450 aag aat cta gat gca ata acc acc cct gac cca acc aca aat gcc agc     1494
Lys Asn Leu Asp Ala Ile Thr Thr Pro Asp Pro Thr Thr Asn Ala Ser
        455                 460                 465 ctg ctg acg aag ctg cag gca cag aac cag tgg ctg cag gac atg aca     1542
Leu Leu Thr Lys Leu Gln Ala Gln Asn Gln Trp Leu Gln Asp Met Thr
    470                 475                 480 act cat ctc att ctg cgc agc ttt aag gag ttc ctg cag tcc agc ctg     1590
Thr His Leu Ile Leu Arg Ser Phe Lys Glu Phe Leu Gln Ser Ser Leu
485                 490                 495                 500 agg gct ctt cgg caa atg tagcatgggc accgtcgac                        1627
Arg Ala Leu Arg Gln Met
                505

<210> SEQ ID NO 2
<211> LENGTH: 525
<212> TYPE: PRT
<213> ORGANISM: Unknown
<220> FEATURE:
```

-continued

<223> OTHER INFORMATION: A conjugate comprising two polypeptides with a mutual affinity

<400> SEQUENCE: 2

```
Met Leu Ala Val Gly Cys Ala Leu Leu Ala Leu Leu Ala Ala Pro
             -15                 -10                  -5

Gly Ala Ala Leu Ala Pro Arg Arg Cys Pro Ala Gln Glu Val Ala Arg
         -1   1               5                  10

Gly Val Leu Thr Ser Leu Pro Gly Asp Ser Val Thr Leu Thr Cys Pro
         15                  20                  25

Gly Val Glu Pro Glu Asp Asn Ala Thr Val His Trp Val Leu Arg Lys
 30                  35                  40                  45

Pro Ala Ala Gly Ser His Pro Ser Arg Trp Ala Gly Met Gly Arg Arg
                 50                  55                  60

Leu Leu Leu Arg Ser Val Gln Leu His Asp Ser Gly Asn Tyr Ser Cys
             65                  70                  75

Tyr Arg Ala Gly Arg Pro Ala Gly Thr Val His Leu Leu Val Asp Val
         80                  85                  90

Pro Pro Glu Glu Pro Gln Leu Ser Cys Phe Arg Lys Ser Pro Leu Ser
 95                 100                 105

Asn Val Val Cys Glu Trp Gly Pro Arg Ser Thr Pro Ser Leu Thr Thr
110                 115                 120                 125

Lys Ala Val Leu Leu Val Arg Lys Phe Gln Asn Ser Pro Ala Glu Asp
                130                 135                 140

Phe Gln Glu Pro Cys Gln Tyr Ser Gln Glu Ser Gln Lys Phe Ser Cys
                145                 150                 155

Gln Leu Ala Val Pro Glu Gly Asp Ser Ser Phe Tyr Ile Val Ser Met
                160                 165                 170

Cys Val Ala Ser Ser Val Gly Ser Lys Phe Ser Lys Thr Gln Thr Phe
175                 180                 185

Gln Gly Cys Gly Ile Leu Gln Pro Asp Pro Pro Ala Asn Ile Thr Val
190                 195                 200                 205

Thr Ala Val Ala Arg Asn Pro Arg Trp Leu Ser Val Thr Trp Gln Asp
                210                 215                 220

Pro His Ser Trp Asn Ser Ser Phe Tyr Arg Leu Arg Phe Glu Leu Arg
                225                 230                 235

Tyr Arg Ala Glu Arg Ser Lys Thr Phe Thr Thr Trp Met Val Lys Asp
                240                 245                 250

Leu Gln His His Cys Val Ile His Asp Ala Trp Ser Gly Leu Arg His
                255                 260                 265

Val Val Gln Leu Arg Ala Gln Glu Glu Phe Gly Gln Gly Glu Trp Ser
270                 275                 280                 285

Glu Trp Ser Pro Glu Ala Met Gly Thr Pro Trp Thr Glu Ser Arg Ser
                290                 295                 300

Pro Pro Ala Arg Gly Gly Gly Ser Gly Gly Gly Ser Gly Gly
                305                 310                 315

Gly Gly Ser Val Glu Pro Val Pro Gly Asp Ser Lys Asp Val
            320                 325                 330

Ala Ala Pro His Arg Gln Pro Leu Thr Ser Ser Glu Arg Ile Asp Lys
335                 340                 345

Gln Ile Arg Tyr Ile Leu Asp Gly Ile Ser Ala Leu Arg Lys Glu Thr
350                 355                 360                 365

Cys Asn Lys Ser Asn Met Cys Glu Ser Ser Lys Glu Ala Leu Ala Glu
                370                 375                 380
```

```
Asn Asn Leu Asn Leu Pro Lys Met Ala Glu Lys Asp Gly Cys Phe Gln
            385                 390                 395

Ser Gly Phe Asn Glu Glu Thr Cys Leu Val Lys Ile Ile Thr Gly Leu
        400                 405                 410

Leu Glu Phe Glu Val Tyr Leu Glu Tyr Leu Gln Asn Arg Phe Glu Ser
    415                 420                 425

Ser Glu Glu Gln Ala Arg Ala Val Gln Met Ser Thr Lys Val Leu Ile
430                 435                 440                 445

Gln Phe Leu Gln Lys Lys Ala Lys Asn Leu Asp Ala Ile Thr Thr Pro
            450                 455                 460

Asp Pro Thr Thr Asn Ala Ser Leu Leu Thr Lys Leu Gln Ala Gln Asn
            465                 470                 475

Gln Trp Leu Gln Asp Met Thr Thr His Leu Ile Leu Arg Ser Phe Lys
        480                 485                 490

Glu Phe Leu Gln Ser Ser Leu Arg Ala Leu Arg Gln Met
    495                 500                 505

<210> SEQ ID NO 3
<211> LENGTH: 1612
<212> TYPE: DNA
<213> ORGANISM: Unknown
<220> FEATURE:
<221> NAME/KEY: sig_peptide
<222> LOCATION: (34)..(90)
<220> FEATURE:
<221> NAME/KEY: CDS
<222> LOCATION: (34)..(1593)
<220> FEATURE:
<221> NAME/KEY: mat_peptide
<222> LOCATION: (91)..(1593)
<220> FEATURE:
<223> OTHER INFORMATION: Description of Unknown Organism:A conjugate
      comprising two polypeptides with a mutual
      affinity.

<400> SEQUENCE: 3
gtcgacgcat ggagtggtag ccgaggagga agc atg ctg gcc gtc ggc tgc gcg      54
                                    Met Leu Ala Val Gly Cys Ala
                                                        -15 ctg ctg gct gcc ctg ctg gcc gcg ccg gga gcg gcg ctg gcc cca agg     102
Leu Leu Ala Ala Leu Leu Ala Ala Pro Gly Ala Ala Leu Ala Pro Arg
        -10                 -5                  -1   1 cgc tgc cct gcg cag gag gtg gca aga ggc gtg ctg acc agt ctg cca     150
Arg Cys Pro Ala Gln Glu Val Ala Arg Gly Val Leu Thr Ser Leu Pro
  5                  10                  15                  20 gga gac agc gtg act ctg acc tgc ccg ggg gta gag ccg gaa gac aat     198
Gly Asp Ser Val Thr Leu Thr Cys Pro Gly Val Glu Pro Glu Asp Asn
                25                  30                  35 gcc act gtt cac tgg gtg ctc agg aag ccg gct gca ggc tcc cac ccc     246
Ala Thr Val His Trp Val Leu Arg Lys Pro Ala Ala Gly Ser His Pro
            40                  45                  50 agc aga tgg gct ggc atg gga agg agg ctg ctg ctg agg tcg gtg cag     294
Ser Arg Trp Ala Gly Met Gly Arg Arg Leu Leu Leu Arg Ser Val Gln
        55                  60                  65 ctc cac gac tct gga aac tat tca tgc tac cgg gcc ggc cgc cca gct     342
Leu His Asp Ser Gly Asn Tyr Ser Cys Tyr Arg Ala Gly Arg Pro Ala
    70                  75                  80 ggg act gtg cac ttg ctg gtg gat gtt ccc ccc gag gag ccc cag ctc     390
Gly Thr Val His Leu Leu Val Asp Val Pro Pro Glu Glu Pro Gln Leu
85                  90                  95                 100 tcc tgc ttc cgg aag agc ccc ctc agc aat gtt gtt tgt gag tgg ggt     438
```

-continued

| | | | |
|---|---|---|---|
| Ser Cys Phe Arg Lys Ser Pro Leu Ser Asn Val Val Cys Glu Trp Gly<br>105 110 115 | | | |
| cct cgg agc acc cca tcc ctg acg aca aag gct gtg ctc ttg gtg agg<br>Pro Arg Ser Thr Pro Ser Leu Thr Thr Lys Ala Val Leu Leu Val Arg<br>120 125 130 | | | 486 |
| aag ttt cag aac agt ccg gcc gaa gac ttc cag gag ccg tgc cag tat<br>Lys Phe Gln Asn Ser Pro Ala Glu Asp Phe Gln Glu Pro Cys Gln Tyr<br>135 140 145 | | | 534 |
| tcc cag gag tcc cag aag ttc tcc tgc cag tta gca gtc ccg gag gga<br>Ser Gln Glu Ser Gln Lys Phe Ser Cys Gln Leu Ala Val Pro Glu Gly<br>150 155 160 | | | 582 |
| gac agc tct ttc tac ata gtg tcc atg tgc gtc gcc agt agt gtc ggg<br>Asp Ser Ser Phe Tyr Ile Val Ser Met Cys Val Ala Ser Ser Val Gly<br>165 170 175 180 | | | 630 |
| agc aag ttc agc aaa act caa acc ttt cag ggt tgt gga atc ttg cag<br>Ser Lys Phe Ser Lys Thr Gln Thr Phe Gln Gly Cys Gly Ile Leu Gln<br>185 190 195 | | | 678 |
| cct gat ccg cct gcc aac atc aca gtc act gcc gtg gcc aga aac ccc<br>Pro Asp Pro Pro Ala Asn Ile Thr Val Thr Ala Val Ala Arg Asn Pro<br>200 205 210 | | | 726 |
| cgc tgg ctc agt gtc acc tgg caa gac ccc cac tcc tgg aac tca tct<br>Arg Trp Leu Ser Val Thr Trp Gln Asp Pro His Ser Trp Asn Ser Ser<br>215 220 225 | | | 774 |
| ttc tac aga cta cgg ttt gag ctc aga tat cgg gct gaa cgg tca aag<br>Phe Tyr Arg Leu Arg Phe Glu Leu Arg Tyr Arg Ala Glu Arg Ser Lys<br>230 235 240 | | | 822 |
| aca ttc aca aca tgg atg gtc aag gac ctc cag cat cac tgt gtc atc<br>Thr Phe Thr Thr Trp Met Val Lys Asp Leu Gln His His Cys Val Ile<br>245 250 255 260 | | | 870 |
| cac gac gcc tgg agc ggc ctg agg cac gtg gtg cag ctt cgt gcc cag<br>His Asp Ala Trp Ser Gly Leu Arg His Val Val Gln Leu Arg Ala Gln<br>265 270 275 | | | 918 |
| gag gag ttc ggg caa ggc gag tgg agc gag tgg agc ccg gag gcc atg<br>Glu Glu Phe Gly Gln Gly Glu Trp Ser Glu Trp Ser Pro Glu Ala Met<br>280 285 290 | | | 966 |
| ggc acg cct tgg aca gaa tcc agg agt cct cca gct cga gga ggt gga<br>Gly Thr Pro Trp Thr Glu Ser Arg Ser Pro Pro Ala Arg Gly Gly Gly<br>295 300 305 | | | 1014 |
| ggt tct gga ggt gga ggt tct gtc gag cca gta ccc cca gga gaa gat<br>Gly Ser Gly Gly Gly Gly Ser Val Glu Pro Val Pro Pro Gly Glu Asp<br>310 315 320 | | | 1062 |
| tcc aaa gat gta gcc gcc cca cac aga cag cca ctc acc tct tca gaa<br>Ser Lys Asp Val Ala Ala Pro His Arg Gln Pro Leu Thr Ser Ser Glu<br>325 330 335 340 | | | 1110 |
| cga att gac aaa caa att cgg tac atc ctc gac ggc atc tca gcc ctg<br>Arg Ile Asp Lys Gln Ile Arg Tyr Ile Leu Asp Gly Ile Ser Ala Leu<br>345 350 355 | | | 1158 |
| aga aag gag aca tgt aac aag agt aac atg tgt gaa agc agc aaa gag<br>Arg Lys Glu Thr Cys Asn Lys Ser Asn Met Cys Glu Ser Ser Lys Glu<br>360 365 370 | | | 1206 |
| gca ctg gca gaa aac aac ctg aac ctt cca aag atg gct gaa aaa gat<br>Ala Leu Ala Glu Asn Asn Leu Asn Leu Pro Lys Met Ala Glu Lys Asp<br>375 380 385 | | | 1254 |
| gga tgc ttc caa tct gga ttc aat gag gag act tgc ctg gtg aaa atc<br>Gly Cys Phe Gln Ser Gly Phe Asn Glu Glu Thr Cys Leu Val Lys Ile<br>390 395 400 | | | 1302 |
| atc act ggt ctt ttg gag ttt gag gta tac cta gag tac ctc cag aac<br>Ile Thr Gly Leu Leu Glu Phe Glu Val Tyr Leu Glu Tyr Leu Gln Asn<br>405 410 415 420 | | | 1350 |

```
aga ttt gag agt agt gag gaa caa gcc aga gct gtg cag atg agt aca    1398
Arg Phe Glu Ser Ser Glu Glu Gln Ala Arg Ala Val Gln Met Ser Thr
            425                 430                 435 aaa gtc ctg atc cag ttc ctg cag aaa aag gca aag aat cta gat gca    1446
Lys Val Leu Ile Gln Phe Leu Gln Lys Lys Ala Lys Asn Leu Asp Ala
        440                 445                 450 ata acc acc cct gac cca acc aca aat gcc agc ctg ctg acg aag ctg    1494
Ile Thr Thr Pro Asp Pro Thr Thr Asn Ala Ser Leu Leu Thr Lys Leu
    455                 460                 465 cag gca cag aac cag tgg ctg cag gac atg aca act cat ctc att ctg    1542
Gln Ala Gln Asn Gln Trp Leu Gln Asp Met Thr Thr His Leu Ile Leu
470                 475                 480 cgc agc ttt aag gag ttc ctg cag tcc agc ctg agg gct ctt cgg caa    1590
Arg Ser Phe Lys Glu Phe Leu Gln Ser Ser Leu Arg Ala Leu Arg Gln
485                 490                 495                 500 atg tagcatgggc accgtcgac                                           1612
Met
```

<210> SEQ ID NO 4
<211> LENGTH: 520
<212> TYPE: PRT
<213> ORGANISM: Unknown
<220> FEATURE:
<223> OTHER INFORMATION: A conjugate comprising two polypeptides with a
      mutual affinity

<400> SEQUENCE: 4

```
Met Leu Ala Val Gly Cys Ala Leu Leu Ala Ala Leu Leu Ala Ala Pro
                -15                 -10                  -5

Gly Ala Ala Leu Ala Pro Arg Arg Cys Pro Ala Gln Glu Val Ala Arg
         -1   1               5                  10

Gly Val Leu Thr Ser Leu Pro Gly Asp Ser Val Thr Leu Thr Cys Pro
         15                  20                  25

Gly Val Glu Pro Glu Asp Asn Ala Thr Val His Trp Val Leu Arg Lys
 30                  35                  40                  45

Pro Ala Ala Gly Ser His Pro Ser Arg Trp Ala Gly Met Gly Arg Arg
                 50                  55                  60

Leu Leu Leu Arg Ser Val Gln Leu His Asp Ser Gly Asn Tyr Ser Cys
             65                  70                  75

Tyr Arg Ala Gly Arg Pro Ala Gly Thr Val His Leu Leu Val Asp Val
             80                  85                  90

Pro Pro Glu Glu Pro Gln Leu Ser Cys Phe Arg Lys Ser Pro Leu Ser
     95                 100                 105

Asn Val Val Cys Glu Trp Gly Pro Arg Ser Thr Pro Ser Leu Thr Thr
110                 115                 120                 125

Lys Ala Val Leu Leu Val Arg Lys Phe Gln Asn Ser Pro Ala Glu Asp
                130                 135                 140

Phe Gln Glu Pro Cys Gln Tyr Ser Gln Glu Ser Gln Lys Phe Ser Cys
                145                 150                 155

Gln Leu Ala Val Pro Glu Gly Asp Ser Ser Phe Tyr Ile Val Ser Met
            160                 165                 170

Cys Val Ala Ser Ser Val Gly Ser Lys Phe Ser Lys Thr Gln Thr Phe
175                 180                 185

Gln Gly Cys Gly Ile Leu Gln Pro Asp Pro Pro Ala Asn Ile Thr Val
190                 195                 200                 205

Thr Ala Val Ala Arg Asn Pro Arg Trp Leu Ser Val Thr Trp Gln Asp
                210                 215                 220
```

```
Pro His Ser Trp Asn Ser Ser Phe Tyr Arg Leu Arg Phe Glu Leu Arg
            225                 230                 235

Tyr Arg Ala Glu Arg Ser Lys Thr Phe Thr Thr Trp Met Val Lys Asp
        240                 245                 250

Leu Gln His His Cys Val Ile His Asp Ala Trp Ser Gly Leu Arg His
        255                 260                 265

Val Val Gln Leu Arg Ala Gln Glu Glu Phe Gly Gln Gly Glu Trp Ser
270                 275                 280                 285

Glu Trp Ser Pro Glu Ala Met Gly Thr Pro Trp Thr Glu Ser Arg Ser
            290                 295                 300

Pro Pro Ala Arg Gly Gly Gly Ser Gly Gly Gly Ser Val Glu
            305                 310                 315

Pro Val Pro Pro Gly Glu Asp Ser Lys Asp Val Ala Ala Pro His Arg
            320                 325                 330

Gln Pro Leu Thr Ser Ser Glu Arg Ile Asp Lys Gln Ile Arg Tyr Ile
        335                 340                 345

Leu Asp Gly Ile Ser Ala Leu Arg Lys Glu Thr Cys Asn Lys Ser Asn
350                 355                 360                 365

Met Cys Glu Ser Ser Lys Glu Ala Leu Ala Glu Asn Asn Leu Asn Leu
            370                 375                 380

Pro Lys Met Ala Glu Lys Asp Gly Cys Phe Gln Ser Gly Phe Asn Glu
        385                 390                 395

Glu Thr Cys Leu Val Lys Ile Ile Thr Gly Leu Leu Glu Phe Glu Val
            400                 405                 410

Tyr Leu Glu Tyr Leu Gln Asn Arg Phe Glu Ser Ser Glu Glu Gln Ala
        415                 420                 425

Arg Ala Val Gln Met Ser Thr Lys Val Leu Ile Gln Phe Leu Gln Lys
430                 435                 440                 445

Lys Ala Lys Asn Leu Asp Ala Ile Thr Thr Pro Asp Pro Thr Thr Asn
            450                 455                 460

Ala Ser Leu Leu Thr Lys Leu Gln Ala Gln Asn Gln Trp Leu Gln Asp
            465                 470                 475

Met Thr Thr His Leu Ile Leu Arg Ser Phe Lys Glu Phe Leu Gln Ser
            480                 485                 490

Ser Leu Arg Ala Leu Arg Gln Met
            495                 500

<210> SEQ ID NO 5
<211> LENGTH: 212
<212> TYPE: PRT
<213> ORGANISM: Unknown
<220> FEATURE:
<223> OTHER INFORMATION: Description of Unknown Organism:A conjugate
      comprising two polypeptides with a mutual
      affinity.

<400> SEQUENCE: 5

Met Asn Ser Phe Ser Thr Ser Ala Phe Gly Pro Val Ala Phe Ser Leu
1               5                   10                  15

Gly Leu Leu Leu Val Leu Pro Ala Ala Phe Pro Ala Pro Val Pro Pro
            20                  25                  30

Gly Glu Asp Ser Lys Asp Val Ala Ala Pro His Arg Gln Pro Leu Thr
        35                  40                  45

Ser Ser Glu Arg Ile Asp Lys Gln Ile Arg Tyr Ile Leu Asp Gly Ile
    50                  55                  60

Ser Ala Leu Arg Lys Glu Thr Cys Asn Lys Ser Asn Met Cys Glu Ser
```

-continued

```
                65                  70                  75                  80
Ser Pro Glu Ala Leu Ala Glu Asn Asn Leu Asn Leu Pro Lys Met Ala
                    85                  90                  95

Glu Lys Asp Gly Cys Phe Gln Ser Gly Phe Asn Glu Glu Thr Cys Leu
                100                 105                 110

Val Lys Ile Ile Thr Gly Leu Leu Glu Phe Glu Val Tyr Leu Glu Tyr
            115                 120                 125

Leu Gln Asn Arg Phe Glu Ser Ser Glu Glu Gln Ala Arg Ala Val Gln
        130                 135                 140

Met Ser Thr Lys Val Leu Ile Gln Phe Leu Gln Lys Lys Ala Lys Asn
145                 150                 155                 160

Leu Asp Ala Ile Thr Thr Pro Asp Pro Thr Thr Asn Ala Ser Leu Leu
                165                 170                 175

Thr Lys Leu Gln Ala Gln Asn Gln Trp Leu Glu Asp Met Pro Thr His
                180                 185                 190

Leu Ile Leu Arg Ser Leu Lys Glu Phe Leu Gln Arg Ser Leu Arg Ala
            195                 200                 205

Leu Arg Gln Met
    210

<210> SEQ ID NO 6
<211> LENGTH: 20
<212> TYPE: DNA
<213> ORGANISM: pCDM8 primer

<400> SEQUENCE: 6
taatacgact cactataggg                                              20

<210> SEQ ID NO 7
<211> LENGTH: 25
<212> TYPE: DNA
<213> ORGANISM: sIL-6R primer

<400> SEQUENCE: 7
ccgctcgagc tggaggactc ctgga                                        25

<210> SEQ ID NO 8
<211> LENGTH: 27
<212> TYPE: DNA
<213> ORGANISM: IL-6-5 primer

<400> SEQUENCE: 8
cggctcgagc cagtaccccc aggagaa                                      27

<210> SEQ ID NO 9
<211> LENGTH: 20
<212> TYPE: DNA
<213> ORGANISM: pCDM primer

<400> SEQUENCE: 9
ccacagaagt aaggttcctt                                              20

<210> SEQ ID NO 10
<211> LENGTH: 50
<212> TYPE: DNA
<213> ORGANISM: primer

<400> SEQUENCE: 10
tcgaggaggt ggaggttctg gaggtggagg ttctggaggt ggaggttctg             50
```

```
<210> SEQ ID NO 11
<211> LENGTH: 50
<212> TYPE: DNA
<213> ORGANISM: primer

<400> SEQUENCE: 11
tcgacagaac ctccacctcc agaacctcca cctccagaac ctccacctcc         50

<210> SEQ ID NO 12
<211> LENGTH: 35
<212> TYPE: DNA
<213> ORGANISM: primer

<400> SEQUENCE: 12
tcgaggaggt ggaggttctg gaggtggagg ttctg                         35

<210> SEQ ID NO 13
<211> LENGTH: 35
<212> TYPE: DNA
<213> ORGANISM: primer

<400> SEQUENCE: 13
tcgacagaac ctccacctcc agaacctcca cctcc                         35

<210> SEQ ID NO 14
<211> LENGTH: 19
<212> TYPE: PRT
<213> ORGANISM: Unknown
<220> FEATURE:
<223> OTHER INFORMATION: a signal peptide which is a conjugate
      comprising one of two polypeptides with a mutual affinity

<400> SEQUENCE: 14

Met Leu Ala Val Gly Cys Ala Leu Leu Ala Ala Leu Leu Ala Ala Pro
 1               5                  10                  15

Gly Ala Ala

<210> SEQ ID NO 15
<211> LENGTH: 18
<212> TYPE: PRT
<213> ORGANISM: Unknown
<220> FEATURE:
<223> OTHER INFORMATION: a linker peptide which is a conjugate
      comprising one of two polypeptides with a mutual affinity

<400> SEQUENCE: 15

Arg Gly Gly Gly Gly Ser Gly Gly Gly Gly Ser Gly Gly Gly Gly Ser
 1               5                  10                  15

Val Glu

<210> SEQ ID NO 16
<211> LENGTH: 13
<212> TYPE: PRT
<213> ORGANISM: Unknown
<220> FEATURE:
<223> OTHER INFORMATION: a linker peptide which is a conjugate
      comprising one of two polypeptides with a mutual affinity

<400> SEQUENCE: 16

Arg Gly Gly Gly Gly Ser Gly Gly Gly Gly Ser Val Glu
 1               5                  10

<210> SEQ ID NO 17
<211> LENGTH: 6
```

```
<212> TYPE: DNA
<213> ORGANISM: Unknown
<220> FEATURE:
<223> OTHER INFORMATION: restriction enzyme SalI

<400> SEQUENCE: 17 gtcgac                                                                6
```

CONJUGATE FOR MODIFYING INTERACTIONS BETWEEN PROTEINS

This application is a 371 of PCT/DE97/00458, filed Mar. 7, 1997.

The present invention relates to a conjugate which is suited to influence interactions between proteins, a DNA encoding such a conjugate and the use of the conjugate.

Many processes occurring in an organism are based on interactions between proteins. Examples of such interactions are found in receptors and the ligand binding thereto. However, the interactions between proteins are often unbalanced. This may be due to the fact that individual proteins involved in the interactions are modified, so that their affinity for other proteins which are also involved, is changed. Individual proteins involved in the interactions may also be lacking. This is found e.g. in the case of cells which do not respond to interleukin-6 (IL-6). Such cells have an incomplete interleukin-6 receptor, i.e. this receptor merely comprises the intracellular signal-triggering subunit gp130 but not the extracellular, IL-6-binding subunit (IL-6R).

Many attempts have been made to remedy unbalanced interactions between proteins. For example, this is tried in the case of an incomplete inleukin-6 receptor by administration of IL-6 (50 ng/ml) and soluble IL-6R (sIL-6R) (1280 ng/ml). However, the provision of sIL-6R is expensive and time-consuming, since sIL-6R will only be biologically active if it originates from eukaryotic cells, and the yields therefrom range from 1 to 6 mg sIL-6R/l. Thus, said administration is no suitable means to lastingly remedy the unbalanced interactions in the case of an incomplete interleukin-6 receptor.

Therefore, it is the object of the present invention to provide a product by which unbalanced interactions between proteins can be remedied, particularly in the case of an incomplete interleukin-6 receptor.

According to the invention this is achieved by the subject matters defined in the claims.

Thus, the subject matter of the present invention relates to a conjugate comprising two polypeptides with a mutual affinity, the polypeptides being linked with each other via a linker.

The expression "polypeptides with a mutual affinity" relates to polypeptides of any kind, origin and length, which have an affinity for each other. Two such polypeptides are present in a conjugate according to the invention. One of these polypeptides may be a receptor and the other may be a ligand binding to the receptor. The receptor may be present in the form of its subunit and the functional part thereof, respectively, which are capable to bind the ligand. Likewise, the ligand may be present in the form of its subunit and the functional part thereof, respectively, which are capable to bind the receptor. The receptor is preferably a cytokine receptor, particularly a receptor for lymphokines, monokines, interferons, colony stimulating factors or interleukins. It is especially preferred for the receptor to be an interleukin-6 receptor or a CNTF receptor. The same applies correspondingly to the ligand. It is preferably a cytokine, particularly a lymphokine, monokine, interferon, colony stimulating factor or interleukin. It is especially preferred for the ligand to be a member of the interleukin-6 family, particularly IL-6, IL-11, CNTF, OSM, LIF or CT-1. The receptor and the ligand may comprise wild-type sequences or sequences differing therefrom by one or several nucleotides. As a result, the receptor and the ligand may have improved and/or new properties. For example, improved properties may be represented by the fact that the bond between receptor and ligand is improved. For example, new properties may be represented by the fact that the ligand shows a behavior modified with respect to proteins with which it reacts after binding to the receptor. For example, IL-6 may be modified to the effect that it binds more strongly to the IL-6 receptor, but can no longer activate the protein gp130. In such a case, IL-6 comprises preferably the sequence of FIG. 3 or fragments thereof. The above statements made on a modification of the wild-type sequence of a receptor and a ligand, respectively, apply correspondingly to the other subunits and functional parts thereof, which contribute to a mutual bond.

The expression "linker" refers to linkers of any kind, which are suited to bind polypeptides. Examples of such linkers are bifunctional, chemical cross-linkers, e.g. DPDPB. Moreover, the linker may be a disulfide bridge formed by both polypeptides. In addition, the linker may be a polypeptide.

In a preferred embodiment, an above conjugate is a fusion polypeptide. It may contain the two polypeptides which have a mutual affinity and are fused to each other, and the linker may represent a disulfide bridge formed by the two polypeptides. The linker is preferably a polypeptide which binds the two other polypeptides with each other. Examples of the latter fusion polypeptide are indicated in FIGS. 1 and 2. These fusion polypeptides comprise a human sIL-6R polypeptide, i.e. the extracellular subunit of an interleukin-6 receptor, and a human IL-6 polypeptide, the polypeptides being linked with each other via differing polypeptide linkers. These fusion polypeptides are referred to as H-IL-6. A variation of H-IL-6 which only contains the amino acids Pro 114 to Ala 323 of the sIL-6R polypeptide, is also provided. Furthermore, a variation of H-IL-6 is provided which comprises amino acids 113 to 323 of the sIL-6R polypeptide and amino acids 29 to 212 of the IL-6 polypeptide. In addition, a fusion polypeptide H-IL-6 is provided whose IL-6 polypeptide comprises the sequence of FIG. 3. The sIL-6R polypeptide of this fusion polypeptide comprises a complete sequence and the sequence between amino acids 113 (114) to 323 of an sIL-6R polypeptide, respectively. Besides, a fusion polypeptide is provided which comprises the extracellular subunit of a human CNTF receptor and human CNTF, both polypeptides being linked with each other via a polypeptide linker.

A further subject matter of the present invention relates to a DNA coding for an above fusion polypeptide. The DNA codes preferably for a fusion polypeptide in which both polypeptides with a mutual affinity are linked with each other via a polypeptide linker. An example of the latter DNA is indicated in FIG. 1. This DNA was deposited with the DSM (Deutsche Sammlung von Mikroorganismen und Zellkulturen [German-type collection of micro organisms and cell cultures]) as CDM8-H-IL-6 under DSM 10549 on Feb. 27, 1996.

A DNA according to the invention can be present in a vector and expression vector, respectively. A person skilled in the art is familiar with examples thereof. In the case of an expression vector for *E. coli* these are e.g. pGEMEX, pUC derivatives, pGEX-2T, pET3b and pQE-8. For the expression in yeast, e.g. pY100, Ycpad1 and vectors for *Pichia pastoris* have to be mentioned, the latter being preferred, while for the expression in animal cells, which may be present within an organism or outside thereof, e.g. pKCR, pEFBOS, pCEV4 and pCDM8 have to be indicated, the latter being preferred. The baculovirus expression vector pAcSGHisNT-A is especially suitable for the expression in insect cells. The person skilled in the art will take into consideration that for the expression of a DNA according to the invention, which contains sIL-6R sequences, it is advisable to use vectors which enable an expression in eukaryotic cells.

However, the person skilled in the art is familiar with suitable cells to express a DNA according to the invention, which is present in an expression vector. Examples of such cells comprise the E. coli strains HB101, DH1, x1776, JM101, JM109, BL21 and SG13009, the yeast strain Saccharomyces cerevisiae and Pichia pastoris, the latter being preferred, the animal cells L, 3T3, FM3A, CHO, Vero, HeLa and COS, the latter being preferred, as well as the insect cells sf9.

The person skilled in the art also knows how to insert a DNA according to the invention in an expression vector. In addition, he knows conditions of transforming cells and transfecting cells, respectively, and then cultivating them. He is also familiar with processes of isolating and purifying the fusion polypeptide expressed by the DNA according to the invention.

A further subject matter of the present invention relates to an antibody directed against an above fusion polypeptide. Such an antibody can be prepared by common methods. It may be polyclonal and monoclonal, respectively. For its preparation it is favorable to immunize animals—particularly rabbits or chickens for a polyclonal antibody and mice for a monoclonal antibody—with an above fusion polypeptide. Further "boosters" of the animals can be effected with the same fusion polypeptide. The polyclonal antibody may then be obtained from the animal serum and egg yolk, respectively. For the preparation of the monoclonal antibody, animal spleen cells are fused with myeloma cells.

By means of the present invention it is possible to influence the interactions between proteins. This can be done by administering conjugates according to the invention and by using DNA according to the invention in a gene therapy. In particular, the unbalanced interactions can be remedied in the case of an incomplete interleukin-6 receptor. The present invention distinguishes itself in that it can be used in a cost-effective manner. This manifests itself particularly in the administration of conjugates according to the invention to influence the unbalanced interactions in the case of an incomplete interleukin-6 receptor.

Furthermore, the present invention is suited for the ex vivo expansion of stem cells, particularly human stem cells. In this connection, it is especially remarkable that it is possible by means of a conjugate H-IL-6 according to the invention to obtain more stem cell colonies in the soft agar than possible with the individual components IL-6 and sIL-6R. Thus, the present invention also represents an important contribution to the well-calculated influence of blood cell formation.

By means of a fusion polypeptide H-IL-6 which comprises the sequence of FIG. 3 as IL-6 polypeptide, the present invention also provides a product which is suitable as IL-6 receptor antagonist. Such a product is of great therapeutic significance.

The carrying-out of the present invention can be controlled by the antibodies according to the invention.

BRIEF DESCRIPTION OF THE DRAWING

FIG. 1 shows the amino acid (DNA) sequence of a fusion polypeptide H-IL-6 according to the invention. Sequences for the restriction enzyme SaII) (SEQ ID NO:17) (GTC-GAC), the signal peptide (SEQ ID NO.: 14) (MLAVGCAL-LAALLAAPGAA) and the linker (SEQ ID NO.: 15) (RGGGGSGGGGSGGGGSVE) are indicated. The linker links the COOH terminus of human sIL-6R with the NH$_2$ terminus of human IL-6.

FIG. 2 shows the amino acid (DNA) sequence of a fusion polypeptide H-IL-6 according to the invention. Sequences for the restriction enzyme SaII (SEQ ID NO:17) (GTC-GAC), the signal peptide (SEQ ID NO.: 14) (MLAVGCAL-LAALLAAPGAA) and the linker (SEQ ID NO.: 16) (RGGGGSGGGGSVE) are indicated. The linker links the COOH terminus of human sIL-6R with the NH$_2$ terminus of human IL-6.

FIG. 3 shows the amino acid sequence of the IL-6 polypeptide (SEQ ID NO:5) present in a fusion polypeptide H-IL-6 according to the invention.

Figure 4:
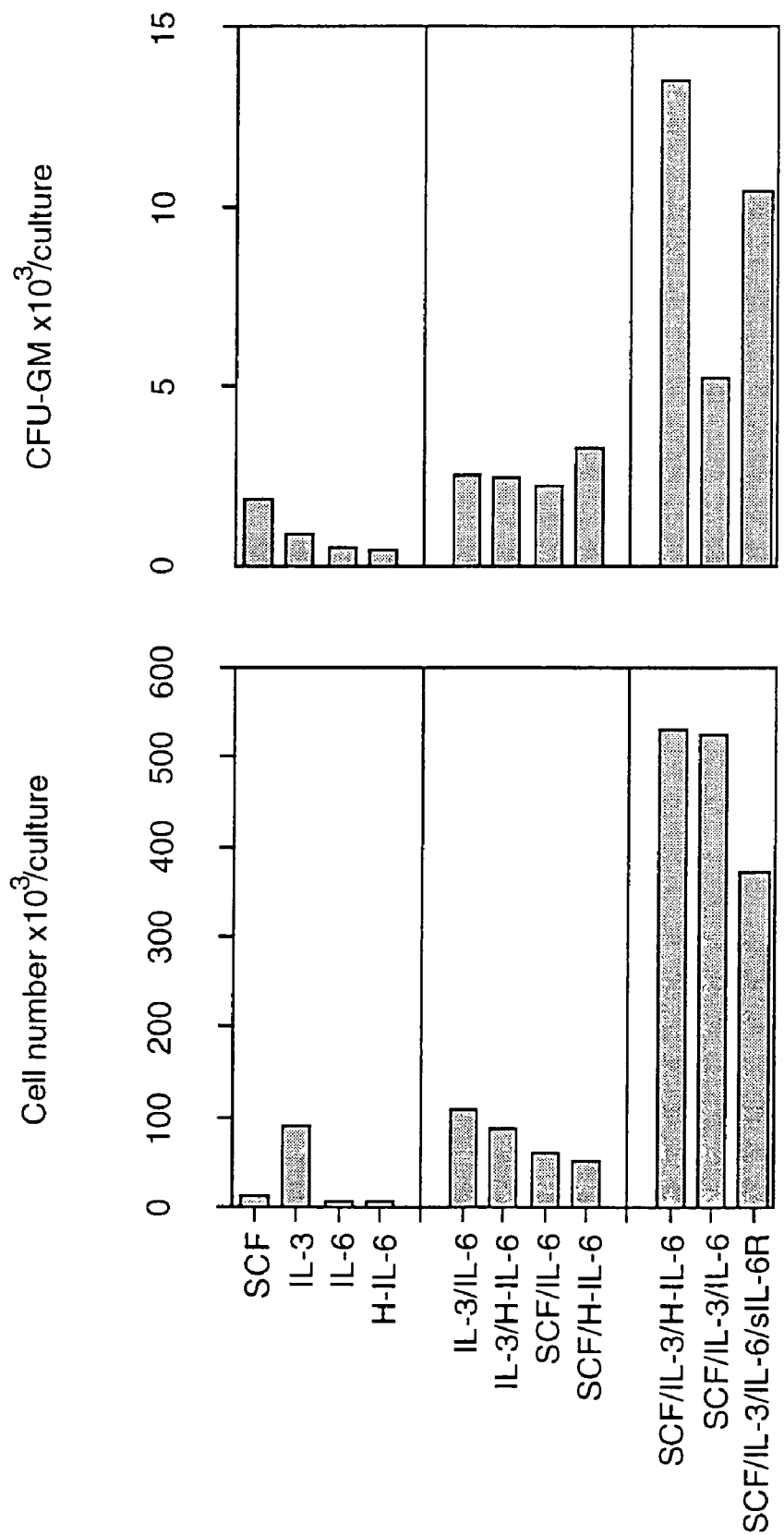
FIG. 4 shows the expansion and colony forming capacities of a fusion polypeptide H-IL-6 according to the invention.

The invention is explained by the below examples.

EXAMPLE 1

Preparation of a DNA According to the Invention

The DNA of FIG. 1 was prepared. For this purpose, human IL-6R cDNA (Schooltink et al., Biochem. J. (1991) 277, 659–664) was used. This cDNA was cloned into the epression plasmid pCDM8 via restriction site Xho I (Müllberg et al., Eur. J. Immunol. (1993) 23, 473–480). By means of a polymerase chain reaction (PCR), an sIL-6R fragment was generated by using the primer (1) (pCDM8 5' primer: 5' TAATACGACTCACTATAGGG 3' (SEQ ID NO:6)) and primer (2) (sIL-6R 3' primer: 5' CCGCTCGAGCTGGAG-GACTCCTGGA 3' (SEQ ID NO:7)) under normal conditions. After being cut with restriction enzymes Hind III and Xho I, this fragment was cloned into the open plasmid pCDM8. The plasmid pCDM8-sIL-6R formed. Thereafter, a second PCR reaction was carried out with IL-6 cDNA which has also been cloned into the expression plasmid pCDM8 by using Xho I. The primers (3) (IL-6-5' primer: 5' CGGCTC-GAGCCAGTACCCCCAGGAGAA3' (SEQ ID NO:8)) and primer (4) (pCDM8 3' primer: 5' CCACAGAAGTAAGGT-TCCTT3' (SEQ ID NO:9)) were used. The PCR product was cut with restriction enzymes Xho I and Not I and cloned into plasmid pCDM8-sIL-6R. The plasmid pCDM8-sIL-6R-IL-6 formed. Thereafter, a synthetic linker was prepared which consisted of two oligonucleotides: primer (5) (5' TCGAG-GAGGTGGAGGTTCTGGAGGTGGAGGTTCTGGAGG-TGGAGGTTCTG 3' (SEQ ID NO:10)) and primer (6) (5' TCGACAGAACCTCCACCTCCAGAACCTCCACCTC-CAGAACCTCCACCTCC3' (SEQ ID NO:11)). Oligonucleotides (5) and (6) were combined according to standard methods into a double strand and then cloned into the plasmid pCDM8-sIL-R-IL-6 digested by the restriction enzyme Xho I. The plasmid pCDM8-H-IL-6 formed.

EXAMPLE 2

Preparation of a DNA According to the Invention

The DNA of FIG. 2 was prepared. For this purpose, the steps as described in Example 1 were carried out. However, the following primers were used instead of primers (5) and (6), respectively: primer (7) (5' TCGAGGAGGTGGAGGT-TCTGGAGGTGGAGGTTCTG 3' (SEQ ID NO:12)) and primer (8) (5' TCGACAGAACCTCCACCTCCAGAAC-CTCCACCTCC 3' (SEQ ID NO:13)). The plasmid pCDM8-H-IL-6-(2) was obtained.

EXAMPLE 3

Expression of a Fusion Polypeptide According to the Invention

COS-7 cells were transfected with pCDM8-H-IL-6 of Example 1 and pCDM8-H-IL-6(2) of Example 2, respectively, by means of electoporation. $10^7$ COS-7 cells were electroporated with 20 μg plasmid by means of a gene pulser (Bio-Rad) at 960 μF and 230 V. 48 h after the transfection, the cells were radioactively labeled metabolically using [$^{35}$S] cysteine/methionine for 4 h and incubated with amino acids which were not labeled radioactively for 2 h. The supernatant from cell lysate and cell supernatant was immunoprecipitated according to standard methods (Müllberg et al., Eur. J. Immunol. (1993) 23, 473–480) using an anti-IL-6 antibody and made visible by autoradiography after SDS gel electrophoresis. Transfected COS-7 cells secreted a 70–75 kDa protein which was recognized by an anti-IL-6 antibody and was not formed by non-transfected cells.

Supernatants of transfected COS-7 cells were separated by SDS gel electrophoresis, transferred to nitrocellulose and detected with an anti-IL-6 antibody. Again, transfected COS-7 cells expressed a 70–75 kDa protein which was recognized by an anti-IL-6 antibody.

Supernatants of transfected COS-7 cells were investigated by means of a commercial ELISA for IL-6 (CLB, Amsterdam, Netherlands) and sIL-6R (Seromed, Gießgen, FRG). H-IL-6 was detected by means of both ELISAs. The concentration of H-IL-6 in the cell supernatant was about 1 μg/ml.

EXAMPLE 4

Stimulation of the Haptoglobin Expression by a Fusion Polypeptide According to the Invention The human hepatoma cell lines HepG2, HepG2-IL-6 and HepG2-PDI were used.

HepG2 cells (ATCC HB 8065) are stimulated to express haptoglobin by IL-6, but not by sIL-6R.

HepG2-IL-6 cells were obtained by stable transfection of HepG2 cells with a human IL-6 expression plasmid. On account of the IL-6 expression these cells down-regulate endogenous IL-6R and thus express no IL-6R. HepG2-IL-6 cells are not stimulated to express haptoglobin by IL-6, but by sIL-6R.

HepG2-PDI cells were obtained by stable transfection of HepG2 cells with a human IL-6 expression plasmid. For this purpose, the expression plasmid included an IL-6 cDNA by which the expressed IL-6 protein included a COOH-terminal retention signal for the endoplasmic reticulum (ER). As a result, these cells did not only retain the expressed IL-6 but also IL-6R in the ER. In contrast to HepG2-IL-6 cells, HepG2-PDI cells do not secrete IL-6 and can only be stimulated to express haptoglobin by a combination of IL-6 and sIL-6R.

The above hepatoma cell lines were cultivated under standard conditions in 96-well cell culture plates (Rose-John et al., J. Biol. Chem. 268 (1993), 22084–22091). The cells were stimulated with IL-6, sIL-6R, IL-6+sIL-6R and cell supernatants, respectively, which originated from COS-7 cells of Example 3, transfected with pCDM8-H-IL-6, pCDM8-H-IL-6(2) and pCDM8, respectively, for 18 h. The cell supernatant was collected and the haptoglobin concentration in the supernatant was determined by means of ELISA (cf. Table 1).

TABLE 1

| Stimulation of the haptoglobin expression | | | | | |
|---|---|---|---|---|---|
| | IL-6 | sIL-6R | IL-6 + sIL-6R | H-IL-6 | control |
| HepG2 | + | − | + + | + + + | − |
| HepG2-IL-6 | − | + + | + + | + + + | − |
| HepG2-PDI | − | − | + + | + + + | − |

It showed that a fusion polypeptide according to the invention, H-IL-6, is capable of stimulating the expression of haptoglobin in cells, i.e. of influencing the interactions between proteins.

EXAMPLE 5

Expansion and Colony Formation of Human CD34$^+$ Cells by a Fusion Polypeptide According to the Invention Cells which express the surface marker CD34 were isolated from human bone marrow and blood of patients whose stem cells had been mobilized by injection of G-CSF, respectively. 6000 of these cells were plated in 3 ml medium in cell culture vessels. After two weeks it turned out that an incubation of the cells with cytokines SCF, IL-3 and H-IL-6 (fusion polypeptide according to the invention) as well as SCF, IL-3 and IL-6 caused strong proliferation. 1000 cells of the resulting cells were plated into new cell culture vessels. After two weeks in a standardized colony induction experiment, the cells treated with SCF, IL-3 and H-IL-6 were capable of forming about three times more colonies than cells treated with SCF, IL-3 and IL-6.

This result shows that cells stimulated by a fusion polypeptide H-IL-6 according to the invention have a greater colony-forming potential than cells stimulated by Il-6 (cf. FIG. 4)

The invention claimed is:

1. A fusion polypeptide comprising a first and second polypeptide, wherein the first polypeptide is a cytokine selected from the group consisting of interleukin-6, interleukin-11, or CNTF, or wherein the first polypeptide is a subunit of interleukin-6, interleukin-11 or CNTF, wherein said subunit can bind an interleukin-6, interleukin-11 or CNTF receptor, and the second polypeptide is an interleukin-6, interleukin-11 or CNTF receptor, or subunit thereof of the receptors, and wherein the receptor subunits can bind their respective cytokines, wherein the first and second polypeptides are linked to each other via a polypeptide linker.

2. The fusion polypeptide according to claim 1, wherein the second polypeptide is a subunit of the cytokine receptor and binds to said cytokine.

3. The fusion polypeptide according to claim 1, wherein the first polypeptide is a subunit of the cytokine and binds to said receptor.

4. The fusion polypeptide according to claim 1, wherein the receptor is an interleukin-6 receptor and the cytokine is interleukin-6.

5. The fusion polypeptide according to claim 1, wherein the cytokine receptor is a CNTF receptor and the cytokine is a CNTF.

6. DNA coding for the fusion polypeptide according to claim 1.

7. An expression plasmid comprising the DNA according to claim 6.

8. An isolated transformant containing the expression plasmid according to claim 7.

9. The fusion polypeptide of claim 1, wherein the receptor is an interleukin-11 receptor and the cytokine is interleukin-11.

10. A composition comprising the fusion polypeptide of claim 1 or the DNA of claim 6, and a pharmaceutically acceptable carrier.

* * * * *